United States Patent [19]
Nepault

[11] Patent Number: 4,698,018
[45] Date of Patent: Oct. 6, 1987

[54] COLLECTOR CUP FOR COLLECTING DENTAL AMALGAM

[76] Inventor: Bernard Nepault, 96 Bis rue Caron, 9100 Athis Mons, France

[21] Appl. No.: 763,141
[22] PCT Filed: Nov. 27, 1984
[86] PCT No.: PCT/FR84/00281
　§ 371 Date: Jul. 29, 1985
　§ 102(e) Date: Jul. 29, 1985
[87] PCT Pub. No.: WO85/02338
　PCT Pub. Date: Jun. 6, 1985

[30] Foreign Application Priority Data
Nov. 29, 1983 [FR] France ............... 83 18989

[51] Int. Cl.⁴ .............................................. A61C 19/00
[52] U.S. Cl. ...................................................... 433/25
[58] Field of Search ................. 433/141, 25, 49, 50, 433/57, 66, 60, 67

[56] References Cited
U.S. PATENT DOCUMENTS
1,896,772  2/1933  Drespel .................................. 433/49
1,966,705  7/1934  Bremer ................................... 109/66
3,283,938  11/1966  Vidal ..................................... 220/20.5

FOREIGN PATENT DOCUMENTS
2024087  8/1970  France .

Primary Examiner—Robert Peshock
Attorney, Agent, or Firm—Fleit, Jacobson, Cohn & Price

[57] ABSTRACT

A dental material collection apparatus includes a vertical cylinder having diametrically opposed notches at an upper end which receive pivot members of a removable collector cup with an eccentric bottom, for holding dental amalgam. After a dentist has finished working with the amalgam, the cup is rotated to an inverted position to discharge waste amalgam into the lower end of the cylinder. A projecting stop on a side of the collector cup adjacent the eccentric bottom engages an upper edge portion of the cylinder, so that the cup can be rotated in only one direction to its discharge position. The lower end of the cylinder is disposed in a frustum-shaped socket-like member with a slip fit. Collector cups may be stored in vertically stacked relationship in a storage device which also includes a cylinder received in a socket-like member, with the cylinder including upper vertically extending slots for receiving the pivot members and stop members of the collector cups.

9 Claims, 5 Drawing Figures

COLLECTOR CUP FOR COLLECTING DENTAL AMALGAM

DESCRIPTION

1. Technical Field

The present invention, a collector cup comprises a hollow vessel or carrier member and a storage column which are joined for use in a dental office or surgery.

In the first instance, it is used as a collector cup for collecting dental amalgam, where the advantage is to eliminate the loss of dental amalgam by means of a novel vessel inverting system.

Secondly, the collector cup for collecting dental amalgam can also hold all other kinds of material in fluid or solid state. In this case, it is a substitute for a conventional Dappen collector which has been used regularly in dental offices.

The storing column is also provided for use jointly with the hollow vessel or carrier member for collecting dental amalgam used also as a Dappen collector.

BACKGROUND ART

We will now explain at the beginning, the first use of the conventional Dappen collector, that is to say, as a collector for collecting amalgam.

Until now the conventional collector used in dental surgery was made simply of separate, interdependent pieces, in which the top part is hollow and holds the amalgam which the practitioner uses.

The amalgam, located in the a hollow cup part of the collector above mentioned, is taken with the help of an amalgam syringe, which deposits the contents into the patient's tooth. This operation is repeated as often as necessary, until the filling up of the hollow of the carious tooth is effected.

Normally, all the amalgam is not used, and as a result, the excess becomes waste that needs to be discarded. With the conventional collector, the excess amalgam is put away by tipping the cup in an uncontrolled way.

The inconvenience of this conventional collector, occurs during the tipping operation to remove and store the amalgam, with the danger that the unused amalgam spills instead of entering the receiver, or other kind of receptacle, thereby causing a danger of environmental pollution. It is also to underline that the traditional system of the above collector has also the inconvenience of allowing release of mercury vapours when the amalgam is not hardened, which is a well-known danger. The inconvenience above mentioned, compels the practitioner or his assistant, to lose time with particular attention to this matter.

DISCLOSURE OF THE INVENTION

The advantage of the present invention is that, the collector cup for collecting Dental Amalgam initialy defined for use in a dental surgery, is composed of a main hollow body (1) with notches (4) provided at its upper part which is connected by pins (7) of a pivoting system which is actuated by means of a handle comprising a knurled wheel or knob (5). The system comprises a carrier member (2) of hemispherical shape or variants thereof, as illustrated, which is provided with a stub (3) preventing the rotation of the vessel or carrier member (2) in an undesired direction. At the lower part of the main body (1) there is provided a hollow, socket-like base plug (6) for the hollow body (1), which is the collector of the excess, unused amalgam. This is done consequently as a result of the pivoting of the carrier member (2) above mentioned.

The above mentioned Collector Cup for Collecting Dental Amalgam is characterized in that the pins (7), the vessel (2) with the stub (3) and the knob or handle (5) may be replaced with an assembly or by separate stocked parts.

The above mentioned collector cup for collecting Dental Amalgam is also characterized by the fact that the pivoting system pins (7) can be also made of rivets.

The above mentioned Collector Cup for Collecting Dental Amalgam also is characterized by the fact that the carrier member (2) at its bottom is narrowed to form a trough of generally hemicylindrical shape with a slight bulge in its bottom at the end adjacent stub (3).

The above mentioned Collector Cup for Collecting Dental Amalgam also is characterized by the fact that the vessel (2) can also be eccentrically mounted in relation to the axial center of the main body (1).

The above mentioned Collector Cup for Collecting Dental Amalgam is also characterized by the fact that the hollow socket-like base plug (6) may be created in various forms and realized in plastic or metal material.

The advantages of the above mentioned invention are attained primarily with the structural arrangement for the controlled inversion of the amalgam wastes towards the hollow, socket-like plug with the pivot system of the amalgam containing, hollow carrier member. Thus, the spilling of the excess amalgam from the vessel or carrier member to the exterior of the storage column is avoided. From this arrangement we also avoid the risk of pollution. It is also to emphasize that when the amalgam has not been hardened, the mercury vapours are isolated from the exterior by the use of the collector cup for amalgam, an object of the present invention, because the vapours remain in the interior of the ensemble of the above mentioned collector cup.

Another advantage of the collector cup for amalgam, the object of this invention, consist of the interchangeability of the pivotinlg means in relation to the main body, which represents a reduction of expenses, because by this way, it is not necessary to replace all of the units of the collector cup.

The invention will now be explained by way of example of the realisation with the help of the annexed drawing in which the figures are as a follows:

BEST MODE FOR CARRING OUT THE INVENTION

Figure 1:
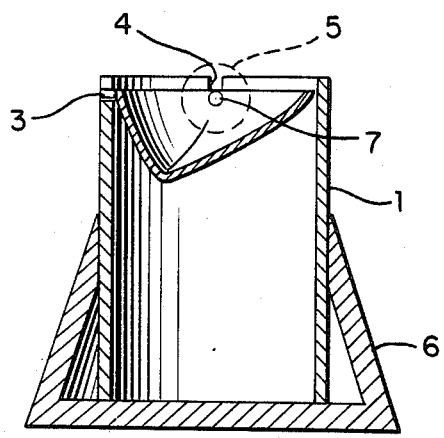
FIG. 1 shows a general cross section of the collector cup assembly for amalgam.
Figure 2:
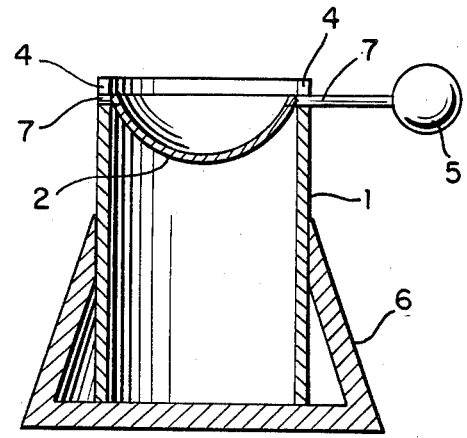
FIG. 2 refers to a lateral cross section of the collector cup assembly for amalgam as shown in FIG. 1.

The collector cup for amalgam as is represented in FIGS. 1 and 2, shows the main hollow body (1) with its hollow, socket-like base plug (6) located at the lower part of the columnar, main hollow body (1). In the upper part of the main hollow body (1) of the above mentioned collector cup for collecting amalgam is located the pivoting means (7) and vessel or carrier member (2), preferably of stainless steel.

Figure 3:
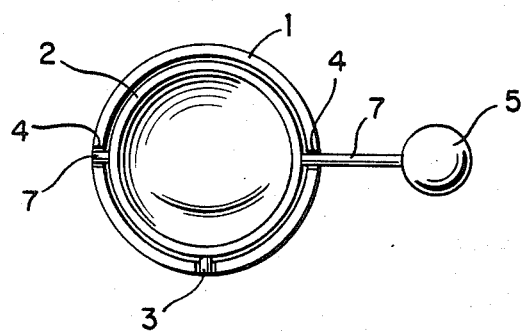
FIG. 3 is a top view of FIG. 2 with a hollow, frustrum-shaped socket-like plug of the collector cup assembly removed.

Relating more details, it is observed that the hollow, socket-like, base plug (6) is useful as a socket for the main body (1). The pivoting means, shown in more detail in FIG. 3, comprises pins (7) that can be made in different shapes and materials, including rivets. Pins 7 are journaled in notches (4) located in the upper part of the main body (1). This arrangement has the advantage of providing a pivoting means that can be removed, when necessary, by simply disengaging pins (7) from their notches (4) and by replacement with a new pivoting means by their introduction in the above mentioned notches (4).

The pivoting means assembly includes a vessel or carrier member (2) in which are incorporated the two pins (7) located in the same line and being opposite one another. Often, the pins (7) are formed by rivets. At the extremity of one of the pins (7) is located a handle or knurled knob (5), desirably for the rotation of the vessel (2). This knob or handle may be of various forms.

Now we will explain the method for using the Collector Cup for Collecting Dental Amalgam, the object of the present invention.

After the amalgam has been prepared with the help of an amalgamator (not represented in the present invention) the practitioner deposits the amalgam in the vessel (2) and takes the necessary quantity with the help of the amalgam syringe. The amalgam is deposited in the tooth as many times as is necessary.

After the filling of the dental hollow is finished, the practitioner saves the excess amalgam, and then, the present invention becomes beneficial in the following operation:

The practitioner by rotating a half turn of the vessel with the help of the knob (5) allows the excess amalgam to fall into the main body (1) base plug (6) assembly. It is to emphasize, that the above mentioned manoeuvre will be repeated until the main body with the plug approaches being full. To empty the socket from the wasted amalgam it is sufficient to pull out the above frustrum-shaped collector socket-like plug (6), which receives the main body (1) with a slip fit. After that, the socket-like plug (6) will be replaced, and the operation will return to the initial phase. Secondly, we are going to explain the second use of the above mentioned invention.

The collector previously explained as collector cup for collecting dental amalgam, can also be used to receive all kinds of liquid or solid material (other than amalgam) used in the dental skill. It will be used in that case, as Dappen collector, employed regularly in dental surgery.

Indeed, until now, employed in dental surgery, are conventional collectors generally called Dappen, which are small tinted glass receptacles perceived to be for the same purpose as that of the collector cup of the present invention, and which is put in the dirty section after use, in order to be cleaned.

The inconvenience of this conventional Dappen Collector is after all in the use and storage, which is a problem, because in the practice of dental skills, often various of these collectors are needed for a work day.

The conventional Dappen Collectors, are taken out for use from the desk, for example, to be put at the disposal of the practitioner on the work table, which is a loss of time and space.

The advantage of the present invention results from the use of the collector cup for collecting dental amalgam in the meantime as a Dappen collector.

The advantages of the present invention will be as follows:

Space saving, because the "Dappen collector" will not encumber. It is the collector cup for collecting the dental amalgam itself.

It saves time on behalf of the the present invention, because it will be no longer necessary to take out from the desk, a Dappen collector. Because, the collector cup for collecting dental amalgam of the present invention, is already in the work table of the practitioner.

Lower cost, because of the double use of the collector cup for collecting dental amalgam, an object of the present invention.

Finally, improvement in convenience because of the fact that the storage column, which is a part of the present invention, is on the work table of the practitioner or his assistant at their disposal.

Now, we will explain another version of the above mentioned invention.

Conventional collectors for amalgam, sufficient in number, have to be stored in an adequate place, because of the quantity required for one work day, in order to allow for cleaning after utilization.

On the other hand, the conventional Dappen collectors, also requires adequate storage space for a sufficient quantity for a work day, in order to clean them after their utilization.

Figure 4:
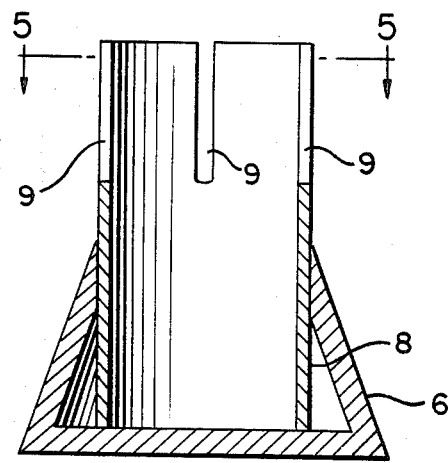
FIG. 4 is cross-sectional representation of a column utilizable as a storage means for a plurality of cup-shaped members.
Figure 5:
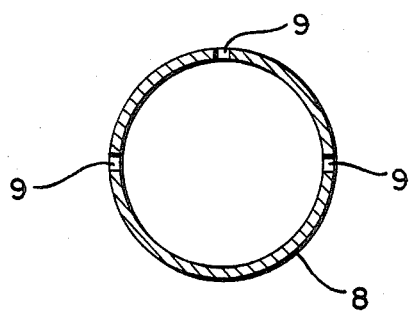
FIG. 5 is a cross sectional view taken along the lines 5—5 of FIG. 4.

The invention for storing the vessels or carrier members consists of a storage column (FIG. 4) provided with a socket, similar in a literal sense, to the socket of the collector cup for collecting dental amalgam, and a hollow main body (8) similar to the collector cup for dental amalgam, but high enough to store fifteen to twenty pivoting carrier-pivot means assemblies.

In order to accomodate the pivoting means and stub, the main hollow body is split with three notches (9) going to the upper edge of the socket of the collector cup in order to stack all the pivoting system, one on top of the other.

This storage column, can take other forms and disposition, and can be made of metal or plastic material.

It is understood, of course, that many constructional alterations may be made in accordance with the invention, without affecting its principle, and with no deviation from the scope of the following claims:

I claim:
1. A dental material collection apparatus comprising,
a hollow, tubular, cylindrical member of right circular cross section having an internal diameter, diametrically opposed notches at an open end of said tubular member,
means for closing an opposite end of said hollow, tubular, cylindrical member;
a hollow carrier member having a circular open end and an outer surface that does not project beyond a position in which the outer surface would interfere with adjacent walls of said cylindrical member when said hollow carrier member is rotated to an inverted discharge position,
diametrically opposed pivot means at said circular open end of said carrier member adapted to be removably journaled in the said notches of said tubular member for allowing a rotation of said hollow carrier member from a material receiving position to an inverted, discharge position to allow any material within said hollow carrier member to be deposited in said tubular member, and stop means projecting from said circular open end of said carrier member for engagement with said cylindrical member, for inhibiting a rotation of said carrier member in only one direction to its inverted position.

2. Apparatus as defined in claim 1 including a handle operatively connected with said carrier member for effecting rotation thereof.

3. An apparatus as defined in claim 1 wherein said stop means comprises a stub on said carrier member for engaging the open end of said tubular cylindrical member.

4. An apparatus as defined in claim 1 wherein said pivot means comprises rivets.

5. An apparatus as defined in claim 1 wherein said carrier member and said tubular member fit sufficiently tight to inhibit gas escape from said tubular member.

6. An apparatus as defined in claim 1 wherein said carrier member deviates from a hemisphere by having a shallow to deep profile such that an eccentric bulge is caused to be located opposite said circular open end.

7. An apparatus as defined in claim 6 wherein said bulge is located proximate to said stop means.

8. the dental material collection apparatus as recited in claim 1, wherein:
said end-closing means is a frustrum-shaped socket-like member for receiving said cylindrical member with a slip fit.

9. A dental material collection apparatus comprising:
a hollow, tubular, cylindrical member of right circular cross section having an internal diameter, slots located at an open end of said tubular member, means for closing an opposite end of said hollow, tubular, cylindrical member;

at least one hollow vessel having a circular open end and an outer surface that does not project beyond a position in which the outer surface would interfere with adjacent walls of said cylindrical member when said vessel is rotated to an inverted discharge position, diametrically opposed pivot means integrally connected with said hollow vessel and projecting therefrom, and a stub means connected with said vessel, said stub means projecting therefrom, each of said means projecting from said vessel having a corresponding slot in said tubular member such that a series of said vessels can be accommodated in a stacked relationship in said tubular member.

* * * * *